US00PP08248P

United States Patent [19]

Meilland

[11] Patent Number: Plant 8,248

[45] Date of Patent: Jun. 8, 1993

[54] ROSE PLANT—MEINOMAD VARIETY

[75] Inventor: Alain A. Meilland, Antibes, France

[73] Assignee: The Conard-Pyle Company, West Grove, Pa.

[21] Appl. No.: 810,182

[22] Filed: Dec. 19, 1991

[51] Int. Cl.[5] ..... A01H 5/00

[52] U.S. Cl. ..... Plt./11

[58] Field of Search ..... Plt. 11, 12, 13, 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and substantially continuously forms attractive double long-lasting bicolored blossoms which are Buttercup Yellow and are more or less edged and suffused with Cardinal Red coloration. The blossoms possess a slight fragrance. The plant exhibits a semi-erect growth habit, forms very vigorous vegetation, and forms attractive shiny dark green foliage which contrasts well with the blossoms. The plant exhibits good disease resistance, and is particularly suited for growing in parks and gardens.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Sonia variety (U.S. Plant Pat. No. 3,095) by the Rumba variety (U.S. Plant Pat. No. 1,919). In Europe the Sonia variety sometimes is known as the Sweet Promise variety. The male parent (i.e., the pollen parent) was the product of the pollination of the Piccadilly variety (non-patented in the United States) by the Johnago variety (non-patented in the United States). The parentage of the new variety can be summarized as follows:

(Sonia × Rumba) × (Piccadilly × Johnago).

The seeds resulting from the above pollination were sown and 23 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting double bicolored blossoms which are Buttercup Yellow and are more or less edged and suffused with Cardinal Red coloration,
(b) forms blossoms which possess a slight fragrance,
(c) forms attractive shiny dark green foliage,
(d) forms very vigorous vegetation,
(e) exhibits a semi-erect growth habit,
(f) is particularly suited for growing in parks and gardens, and
(g) is not particularly affected by cryptogamic diseases.

The new variety has been found to undergo asexual propagation by a number of routes, including budding, grafting, cuttage, etc. The characteristics of the new variety have been found to be strictly transmissible by such asexual propagation from one generation to another in France.

The new variety has been named the Meinomad variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing outdoors at Le Cannet des Maures, Var, France.

FIG. 1 illustrates a specimen of a young shoot;

FIG. 2 illustrates a speciman of a floral bud before the opening of the sepals;

FIG. 3 illustrates a specimen of a floral bud at the opening of the sepals;

FIG. 4 illustrates a specimen of a floral bud at the opening of the petals;

FIG. 5 illustrates a specimen of a flower in the course of opening;

FIG. 6 illustrates a specimen of an open flower — plan view — obverse;

FIG. 7 illustrates a specimen of an open flower — plan view — reverse;

FIG. 8 illustrates a specimen of a fully open flower — plan view — obverse;

FIG. 9 illustrates a specimen of a fully open flower — plan view — reverse;

FIG. 10 illustrates a specimen of a floral receptacle showing the arrangement of the stamens and pistils;

FIG. 11 illustrates a specimen of a floral receptacle showing the arrangement of the pistils (stamens removed);

FIG. 12 illustrates a specimen of a flowering stem;

FIG. 13 illustrates a specimen of a main branch;

FIG. 14 illustrates a specimen of a leaf with three leaflets — plan view — upper surface;

FIG. 15 illustrates a specimen of a leaf with five leaflets — plan view — lower surface; and FIG. 16 illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of two year old plants made during June while budded on *Rosa froebelli* understock and growing outdoors at Le Cannet des Maures, Var, France. The coloration in common terms precedes reference to the chart.

Class: Hybrid Tea.

Plant:

*Height.*—Approximately 90 to 100 cm. habit — semi-erect.

Branches:

*Color.*—Young stems: medium green, Green Group 143B and very widely stained with reddish coloration. Adult wood: medium green, Green Group 143A.

*Thorns.*—*Size: fairly large. Quantity: fairly numerous. Color: reddish on young stems and greenish-pink on mature wood.*

Leaves:

*Stipules.*—Adnate, pectinate, very wide and linear.

*Petioles.*—Upper surface: striped reddish brown on young foliage and medium green on mature foliage with glandular edges. Under surface: light green, and bear very few prickles.

*Leaflets.*—Number: 3, 5 (most often), and sometimes 7. Shape: elliptic to oval. Serration: single and regular. Texture: very Leathery. General appearance: very dense, dark and very shiny foliage. Color (young foliage): Upper surface: dark green, Yellow-Green Group 147A, more or less stained with reddish coloration. Under surface: dark green, Yellow-Green Group 147B, more or less stained with reddish coloration. Color (adult foliage): Upper surface: dark green, Yellow-Green Group 147A. Under surface: medium green, Yellow-Green Group 147B.

Inflorescence:

*Number of flowers.*—Usually a single bloom per stem, however, sometimes up to 4 blooms per stem form.

*Peduncle.*—Light green and widely stained with reddish coloration, bears numerous prickles mixed with glandular acicules. The length is approximately 5 to 12 cm. on average.

*Sepals.*—Upper surface: light green, widely stained with reddish coloration.

*Buds.*—Shape: conical. Length: approximately 4 cm. on average. Size: Large. Color upon opening: Upper surface: Lemon Yellow, Yellow-Orange Group 14B. Under surface: Chrome Yellow, Yellow-Orange Group 15C, very widely stained with light Cherry Red, Red Group 45C.

*Flower.*—Shape: cup-like, double. Diameter: approximately 14 cm. on average. Color (when opening begins): Upper surface: Buttercup Yellow, Yellow-Orange Group 15B, turning to medium Lemon Yellow, Yellow-Orange Group 14B on the outer petals, more or less stained and edged with Cardinal Red, Red Group 53B, and becoming lighter towards the inside. Under surface: Chrome Yellow, Yellow-Chrome Group 15C, turning to Barium Yellow, Yellow Group 10B on the outer petals and more or less suffused with light Cardinal Red, Red Group 53D. Color (when blooming): Upper surface: Buttercup Yellow, Yellow-Orange Group 15B, turning to medium Lemon Yellow, Yellow-Orange Group 14B on the outer petals, more or less widely edged with Cardinal Red, Red Group 53B, and becoming lighter towards the inside. Under surface: Chrome Yellow, Yellow-Orange 15C, turning to Barium Yellow, Yellow Group 10B on the outer petals, and more or less suffused with light Cardinal Red, Red Group 53D. Color (at end of opening): Upper surface: Buttercup Yellow, Yellow-Orange Group 15B, turning to medium Lemon Yellow, Yellow-Orange Group 14B on the outer petals, more or less edged and suffused with Cardinal Red, Red Group 53B, and becoming lighter towards the inside. Under surface: Chrome Yellow, Yellow-Orange Group 15C, turning to Barium Yellow, Yellow Group 10B on the outer petals and more or less edged and suffused with light Cardinal Red, Red Group 53D. Fragrance: slight. Lasting quality: long. Petal number: approximately 22 on average. Petal shape: rounded with more or less indented edges. Texture: very consistent. Petal drop: good. Stamen number: approximately 114 on average. Anthers: bright yellow in coloration and commonly located at substantially the same level as the stigma. Filaments: bright yellow and disposed around the pad of the receptacle. Pistils: approximately 105 on average. Stigmas: normal, and yellowish in coloration. Styles: light fuschia in coloration, tomentose and straw colored near the base, and of irregular heights. Receptacle: medium green in coloration, more or less stained with reddish coloration, and in longitudinal section it is wide and in the shape of a pitcher at the dehiscence of the anthers.

Development:

*vegetation.*—Very vigorous.

*Blooming.*—Abundant and fairly continuous.

*Resistance to frost.*—Good.

*Resistance to diseases.*—Good.

I claim:

1. A new and distinct variety of Hybrid Tea rose plant characterized by the following combination of characteristics:

(a) forms in abundance attractive long-lasting double bicolored blossoms which are Buttercup Yellow and are more or less edged and suffused with Cardinal Red coloration,
(b) forms blossoms which possess a slight fragrance,
(c) forms attractive shiny dark green foliage,
(d) forms very vigorous vegetation,
(e) exhibits a semi-erect growth habit,
(f) is particularly suited for growing in parks and gardens, and
(g) is not particularly affected by cryptogamic diseases;

substantially as herein shown and described.

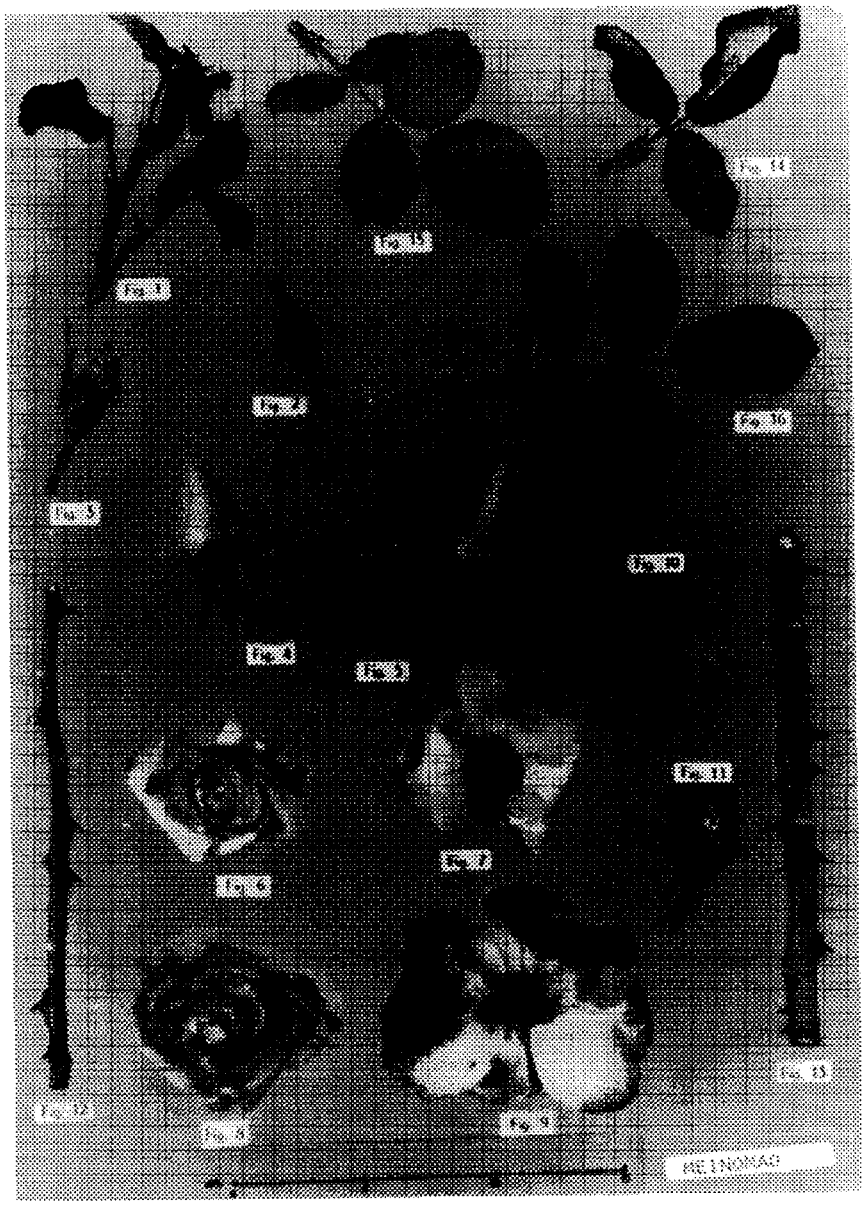

* * * * *